(12) United States Patent
Mason et al.

(10) Patent No.: US 7,645,244 B2
(45) Date of Patent: Jan. 12, 2010

(54) ULTRASOUND SYSTEMS AND METHODS FOR TREATING ISCHEMIC LIMBS OR TISSUE AFFECTED BY PERIPHERAL ARTERIAL DISEASE

(75) Inventors: Martin Mason, Andover, MA (US); Donald J. Brooks, Andover, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 667 days.

(21) Appl. No.: 11/178,244

(22) Filed: Jul. 8, 2005
(Under 37 CFR 1.47)

(65) Prior Publication Data
US 2006/0058709 A1 Mar. 16, 2006

Related U.S. Application Data

(60) Provisional application No. 60/586,591, filed on Jul. 9, 2004.

(51) Int. Cl.
*A61N 7/00* (2006.01)
(52) U.S. Cl. ......................................................... 601/2
(58) Field of Classification Search ...................... 601/2; 600/437–440
See application file for complete search history.

(56) References Cited

U.S. PATENT DOCUMENTS

| | | | | |
|---|---|---|---|---|
| 5,324,255 A | * | 6/1994 | Passafaro et al. | 604/22 |
| 5,520,612 A | * | 5/1996 | Winder et al. | 601/2 |
| 5,957,850 A | * | 9/1999 | Marian et al. | 600/459 |
| 6,296,619 B1 | * | 10/2001 | Brisken et al. | 600/466 |
| 6,425,867 B1 | * | 7/2002 | Vaezy et al. | 600/439 |
| 6,794,369 B2 | | 9/2004 | Newman et al. | |
| 6,945,937 B2 | * | 9/2005 | Culp et al. | 600/437 |
| 2002/0082529 A1 | * | 6/2002 | Suorsa et al. | 601/2 |

* cited by examiner

*Primary Examiner*—Eric F Winakur
(74) *Attorney, Agent, or Firm*—Vista IP Law Group LLP (57) ABSTRACT

A method of treating tissue within a body includes aiming an ultrasound transducer towards target tissue, and delivering ultrasound energy towards the target tissue to thereby reduce pain at the target tissue. A method of treating tissue within a body includes aiming an ultrasound transducer towards target tissue, and delivering ultrasound energy towards the target tissue to increase nitric oxide at the target tissue. An ultrasound system includes a first ultrasound transducer for emitting ultrasound energy from outside a patient, and drive circuitry coupled to the first ultrasound transducer, wherein the drive circuitry is configured to generate a drive signal at a frequency that is between 20 kHz and 100 kHz for the first ultrasound transducer.

15 Claims, 6 Drawing Sheets

ULTRASOUND SYSTEMS AND METHODS FOR TREATING ISCHEMIC LIMBS OR TISSUE AFFECTED BY PERIPHERAL ARTERIAL DISEASE

RELATED APPLICATION DATA

This application claims the benefit of U.S. Provisional Patent Application Ser. No. 60/586,591, filed on Jul. 9, 2004, the entire disclosure of which is expressly incorporated by reference herein.

FIELD

The present invention relates generally to apparatus and methods for treating tissue, and more particularly to apparatus and methods for treating ischemic limbs or tissue affected by peripheral arterial disease.

BACKGROUND

Peripheral arterial disease is the most common form of atherosclerosis that affects many people worldwide. As a result of such disease, many people experience pain during walking. Such condition may be treated medically with exercise and drugs, such as Cilostazol, which modestly improves walking ability by inhibition of platelet aggregation. However, in many cases, patients do not follow the prescribed exercise therapy because of pain associated with the disease. Other types of drugs have also been used to treat ischemia, but many of these drugs have side effects.

Medical interventions such as balloon angioplasty, stenting, and surgery are options to treat patients who are suffering from peripheral arterial diseases and critical limb ischemia. However, many of such procedures may fail. Consequences of graft failure include continued ischemia, poor wound healing, gangrene, or amputation of a patient's limb.

Ultrasound devices have been used to diagnose patients. For example, ultrasonic energy may be employed to obtain images of a part of a patient during a diagnostic procedure. In addition, ultrasound systems have been used for treating tissue, e.g., by directing acoustic energy towards a target tissue region within a patient, such as a cancerous or benign tumor, to heat the tissue region. For example, an ultrasound transducers may be disposed adjacent a patient's body and operated (generally at a frequency that is in the megahertz range) to deliver high intensity acoustic waves, such as ultrasonic waves, at an internal tissue region of a patient to heat the tissue region, thereby injuring target tissue at the tissue region.

SUMMARY

In accordance with some embodiments, a method of treating tissue within a body includes aiming an ultrasound transducer towards target tissue, and delivering ultrasound energy towards the target tissue to thereby reduce pain at the target tissue.

In accordance with other embodiments, a method of treating tissue within a body includes aiming an ultrasound transducer towards target tissue, and delivering ultrasound energy towards the target tissue to increase nitric oxide at the target tissue.

In accordance with other embodiments, an ultrasound system includes a first ultrasound transducer for emitting ultrasound energy from outside a patient, and drive circuitry coupled to the first ultrasound transducer, wherein the drive circuitry is configured to generate a drive signal at a frequency that is between 20 kHz and 100 kHz for the first ultrasound transducer.

Other aspects and features will be evident from reading the following detailed description of the embodiments.

BRIEF DESCRIPTION OF THE DRAWINGS

Various embodiments are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments.

DETAILED DESCRIPTION OF THE EMBODIMENTS

Figure 1:
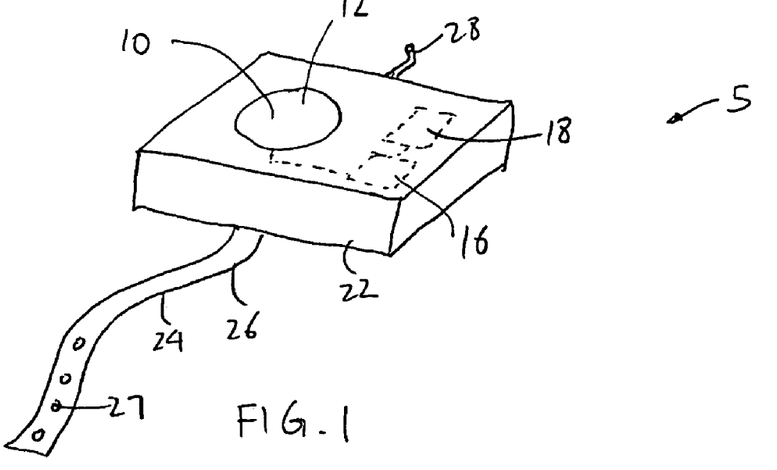
FIG. 1 illustrates an ultrasound system configured to deliver acoustic energy in accordance with some embodiments.

FIG. 1 illustrates an ultrasound system 5 in accordance with some embodiments. The ultrasound system 5 includes an ultrasound transducer 10, a drive circuitry 16 coupled to the transducer 10, and a controller 18 coupled to the drive circuitry 16. The ultrasound system 5 also includes a structure 22 for carrying the transducer 10, the drive circuitry 16, and the controller 18, and a securing device 24 for securing the transducer 10 relative to a patient during use. The transducer 10 is configured to deliver acoustic energy to target tissue located inside the patient. The acoustic energy may be used to increase the level of nitric oxide within the tissue, thereby relieving, or at least reducing, pain in the tissue.

The structure 22 is not limited to the rectangular shape shown, and can be any shapes, forms, and/or configurations in other embodiments, so long as it is capable of providing a platform or area to which the transducer 10 can be secured. The structure 22 may be substantially rigid, semi-rigid, or substantially flexible, and can be made from a variety of materials, such as plastics, polymers, metals, and alloys. Electrodes and conducting wires (not shown) may also be provided in a known manner for coupling the transducer 10 to the driver 16. In the illustrated embodiments, the driver 16 and the controller 18 are secured directly to the structure 22. Alternatively, the driver 16 and/or the controller 18 can be coupled to the structure 22 via a cable. In such cases, the electrodes for the transducer 10 are housed within the structure 22, and exit from the structure 22 for coupling to the driver 16 and/or the controller 18.

In the illustrated embodiments, the transducer 10 includes one or more transducer elements 12 (one is shown). Each of the transducer element(s) 12 may be a one-piece piezoceramic part, or alternatively, be composed of a mosaic arrangement of a plurality of small piezoceramic elements (e.g., phased array). The piezoceramic parts or the piezoceramic elements may have a variety of geometric shapes, such as hexagons, triangles, squares, and the like. The material used to construct the transducer element(s) 12 could be a composite material, a piezoceramic, or any other material that could transform electrical signal into acoustic wave. The transducer element(s) 12 are coupled to the driver 16 and/or controller 18 for generating and/or controlling the acoustic energy emitted by the transducer element(s) 12. For example, the driver 16 may generate one or more electronic drive signals, which may be controlled by the controller 18. The transducer element(s) 12 convert the drive signals into acoustic energy. The controller 18 and/or driver 16 may be separate or integral components. It will be appreciated by one skilled in the art that the operations performed by the controller 18 and/or driver 16 may be performed by one or more controllers, processors, and/or other electronic components, including software and/or hardware components. The terms controller and control circuitry may be used herein interchangeably, and the terms driver and drive circuitry may be used herein interchangeably.

The driver 16, which may be an electrical oscillator, may generate drive signals in the ultrasound frequency spectrum, e.g., as low as ten kilohertz (10 KHz), or as high as five hundred kilohertz (500 kHz). In some embodiments, the driver 16 provides drive signals to the transducer 10 at a frequency that is between about twenty kilohertz to one hundred kilohertz (20-100 kHz). However, in other embodiments, the driver 16 can also be configured to operate in other ranges of frequencies. When the drive signals are provided to the transducer 10, the transducer 10 emits acoustic energy from its surface, as is well known to those skilled in the art.

The controller 18 may control the amplitude, and therefore the intensity or power, of the acoustic wave transmitted by the transducer 10. In other embodiments, if the transducer 10 includes more than one transducer elements 12, the controller 18 may also control a phase component of the drive signals to respective transducer elements 12 of the transducer device 10, e.g., to control a shape or size of a focal zone generated by the transducer elements 12 and/or to move the focal zone to a desired location. For example, the controller 18 may control the phase shift of the drive signals to adjust a focal distance (i.e., the distance from the face of the transducer 10 to the center of the focal zone). In further embodiments, the controller 18 can be configured to operate the transducer 10 for a prescribed duration, such as at least 15 minutes. Alternatively, or additionally, the controller 18 can be configured to automatically turn off the transducer 10 when a usage of the transducer 10 exceeds a prescribed time, such as 60 minutes.

Figures 2, 3:
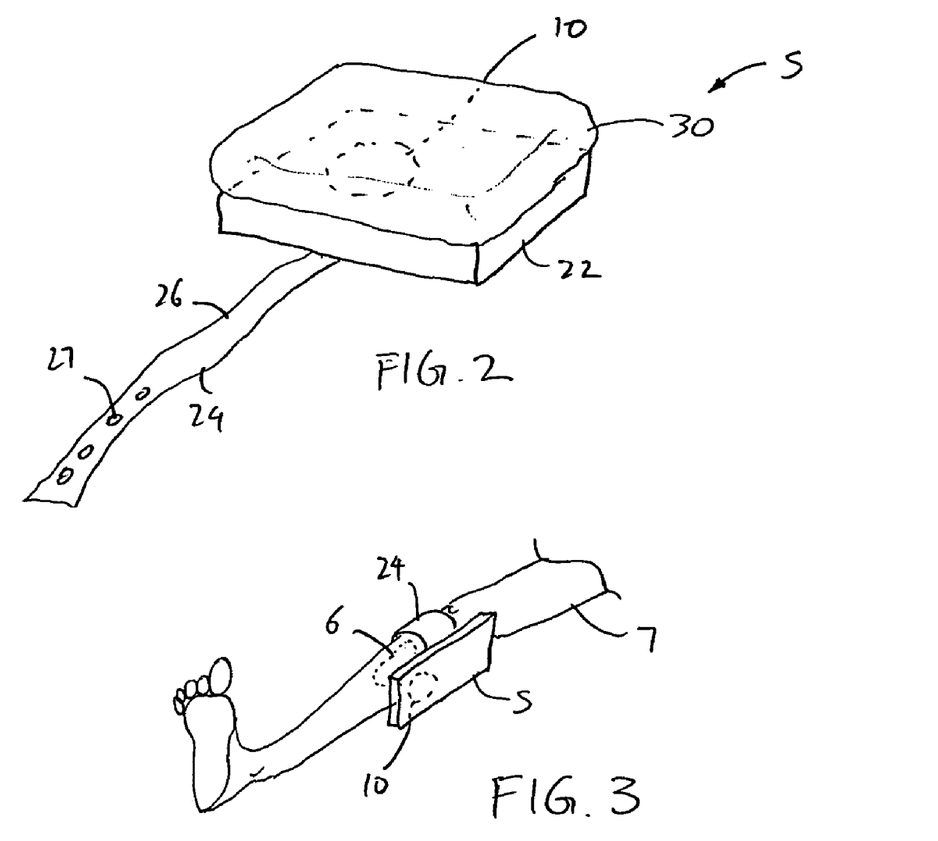
FIG. 2 illustrates a variation of the ultrasound system of FIG. 1, showing the ultrasound system further having a coupling membrane.
FIG. 3 illustrates the ultrasound system of FIG. 1, showing the system being used to treat a patient's leg.

In other embodiments, the system 5 further includes a coupling membrane 30, such as an inflatable body or a balloon, for providing or improving an acoustic coupling between the transducer 10 and a skin of the patient, while ultrasound energy is being delivered (FIG. 2). The coupling membrane 30 can be filled with a fluid, such as degassed water.

FIG. 3 illustrates a method of using the system 5 to treat target tissue 6 within a patient 7 in accordance with some embodiments. In the illustrated embodiments, the target tissue 6 is one that has been affected by a peripheral arterial disease, and is located within a leg of the patient 7. In other embodiments, the target tissue 6 can be associated with other diseases or medical conditions (such as pain due to exercising), and can be located at other parts of the patient 7.

First, the securing device 24 is used to secure the ultrasound transducer 10 relative to the patient 7. As shown in FIG. 1, the securing device 24 includes a strap 26, a plurality of openings 27 on the strap 26, and a pin 28 secured to the structure 22, wherein the pin 28 is sized to mate with a selected one of the openings 27. When using the securing device 24, the strap 26 is tightly wrapped around the leg of the patient 7, and one of the openings 27 is mated with the pin 28, thereby securing the ultrasound transducer 10 directly against a skin on the patient's leg. If the system 5 includes the coupling membrane 30 of FIG. 2, the securing device 24 is used to secure the coupling membrane 30 against the skin on the patient's leg. The coupling membrane 30 functions as an acoustic coupler and provides good contact with the curved leg surface.

Next, the transducer 10 delivers ultrasound energy to the target tissue 6. Particularly, the driver 16 and/or the controller 18 are used to generate and/or to control the acoustic energy emitted by the transducer 10. The transducer 10 may emit acoustic energy in a continuous manner, or alternatively, in pulses. In some embodiments, the driver 16 and/or the controller 18 may also control a phase, an operating frequency, and/or an operating amplitude of the transducer 10.

In the illustrated embodiments, the transducer 10 is operated at a frequency that is between 10 kHz and 500 kHz, and more preferably, at a frequency that is between 20 kHz and 100 kHz. Such frequency range produces low attenuation in the tissue 6 and may allow resonance to occur within the patient's limb (e.g., the leg). The effect of resonance allows the required input energy for the transducer 10 to be decreased. In other embodiments, the transducer 10 can be operated at other frequency ranges.

The delivered acoustic energy by the transducer 10 is at least partially absorbed by the tissue 6 within the patient's leg, and causes mechanical stimulation of endothelial cells by compression and wall shear stress in blood vessels, thereby stimulating production of endothelial nitric oxide syntheses (eNOs). In the illustrated embodiments, the transducer 10 is used for a duration of at least 10 minutes, and more preferably, at least 15 minutes, thereby causing production of eNOs that translates into nitric oxide up-regulation. The heightened level of nitric oxide is believed to have a number of effects on the tissue 6, including inhibition of leukocyte and platelet adhesion, control of vascular tone and maintenance of a thromboresistant interface between the bloodstream and the vessel wall, increase in capillary circumference (vasodilation), and/or increase in blood flow (perfusion). Such effect(s) in turn helps relieve pain at the tissue 6, and allows the patient 7 to rehabilitate through exercise. In other embodiments, the transducer 10 can be operated for other durations that are different from those mentioned previously.

In some embodiments, during a treatment session, the energy intensity or dosage delivered by the transducer 10 at the tissue 6 is kept below a prescribed threshold (e.g., by using appropriate driving scheme and/or by selecting appropriate operation parameters, such as an operating frequency, an operating amplitudes, etc.), thereby protecting the tissue 6 from being injured by the acoustic energy.

After a desired treatment effect is achieved, the transducer 10 is then removed from the patient 7, or vice versa.

Figure 4A:
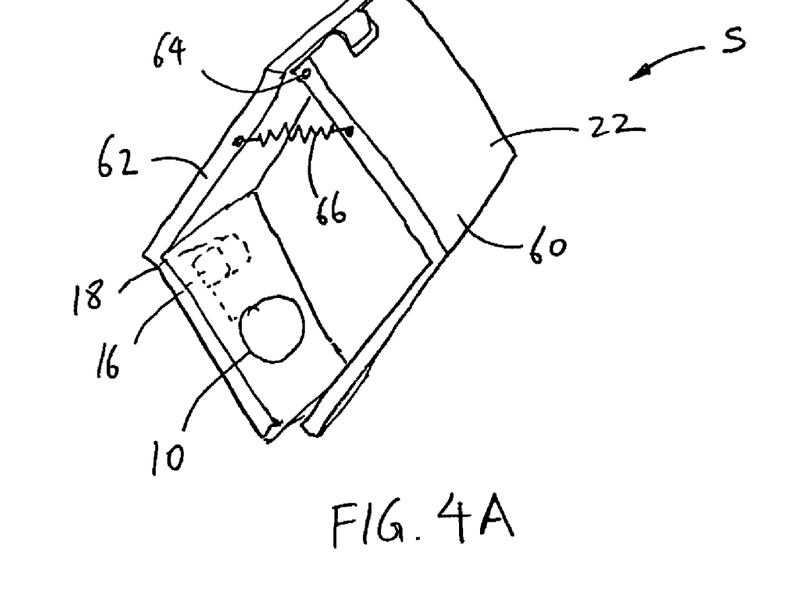
FIG. 4A illustrates an ultrasound system in accordance with other embodiments.
Figure 4B:
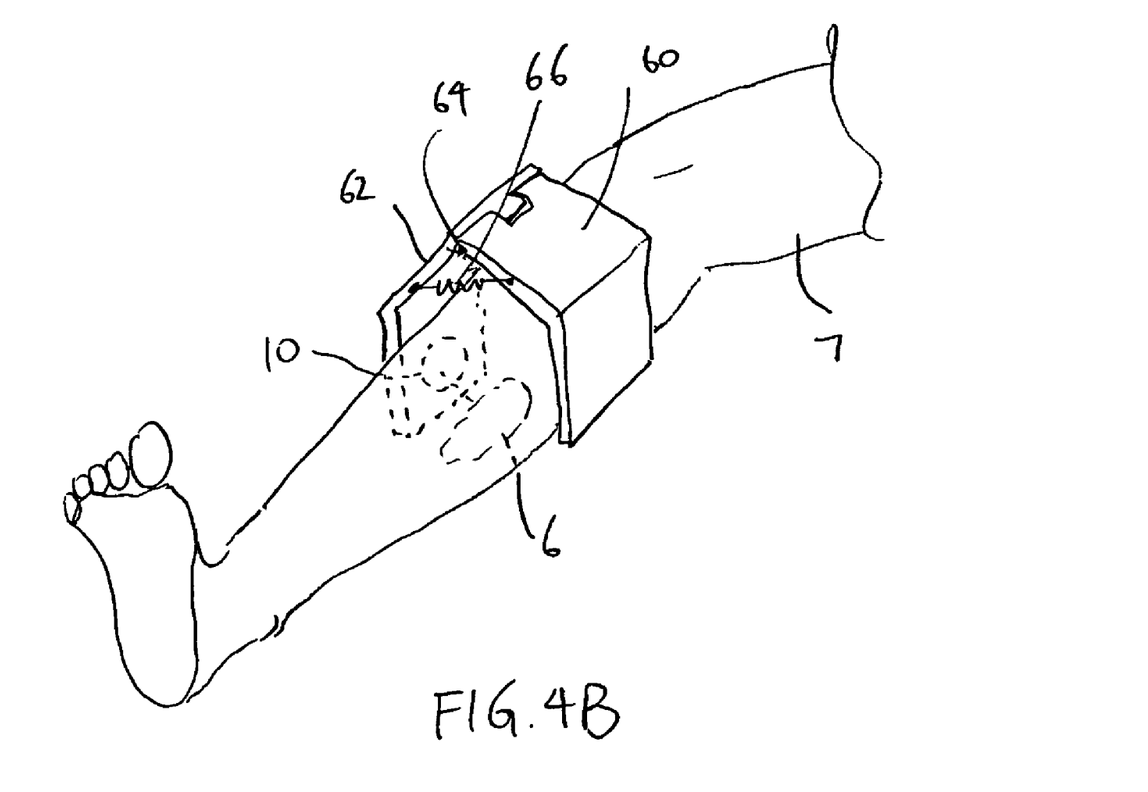
FIG. 4B illustrates the ultrasound system of FIG. 4A, showing the ultrasound system being used to treat a patient's leg.

In the above embodiments, the securing device 24 is described as having the strap 26. However, it should be noted that the securing device 24 is not limited to the example discussed previously, and that the securing device 24 can have other shapes and configurations, as long as it is capable of securing the transducer 10 relative to the patient 7 during use. For example, in other embodiments, the structure 22 includes a first frame 60 and a second frame 62 that is rotatably coupled to the first frame 60 via a shaft 64 (FIG. 4A). In such cases, the securing device 24 includes a spring 66 secured to the first and second frames 60, 62, thereby biasing the frames 60, 62 to have a closed configuration. During use, the frames 60, 62 are pulled apart from each other to provide an opened configuration for the structure 22, and the frames 60, 62 are placed on opposite sides of the patient's leg (FIG. 4B). The spring 64 undergoes tension to pull the frames 60, 62 towards each other, thereby pressing the transducer 10 (or the coupling membrane 30 if one is provided) towards a patient's skin.

Figure 5A:
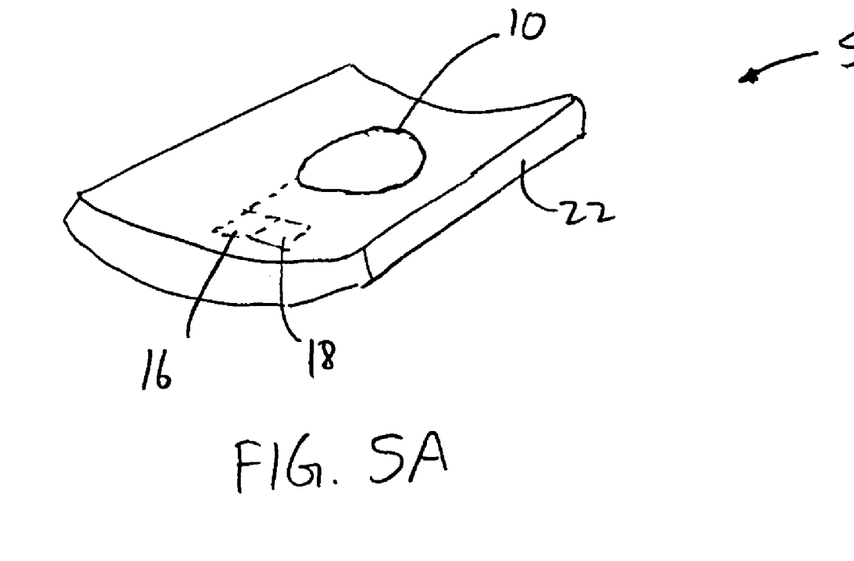
FIG. 5A illustrates an ultrasound system in accordance with other embodiments.
Figure 5B:
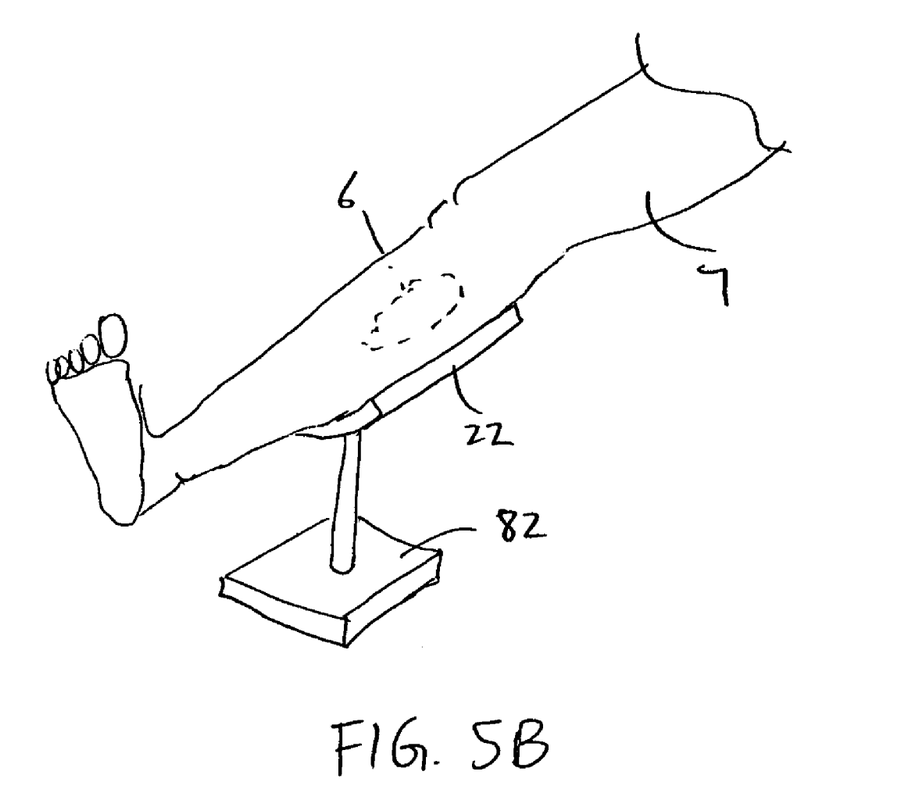
FIG. 5B illustrates the ultrasound system of FIG. 5A, showing the ultrasound system being used to treat a patient's leg.

In other embodiments, the system 5 does not include the securing device 24. For example, in other embodiments, the structure 22 includes a surface 80 for supporting at least a portion of the patient, such as a limb (e.g., an arm or a leg) (FIG. 5A). The surface 80 can have a curvilinear profile or a flat profile. During use, the patient's leg is placed on top of the surface 80. In such cases, the gravitational force pulls the patient's leg towards the structure 22, thereby effecting coupling between the patient's skin and the transducer 10 (or the coupling membrane 30 if one is provided) (FIG. 5B). The structure 22 can be supported by a support stand 82, or alternatively, be placed on a bed during use.

Figure 6A:
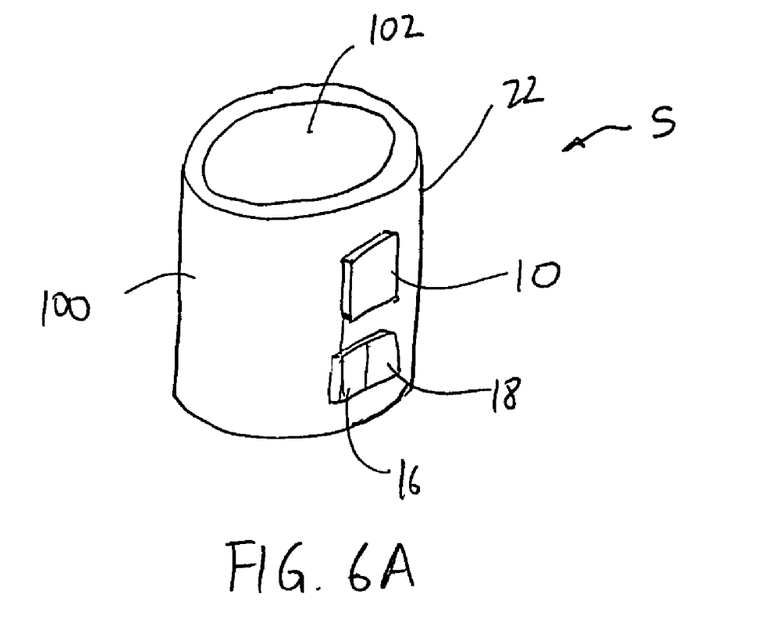
FIG. 6A illustrates an ultrasound system in accordance with other embodiments.
Figure 6B:
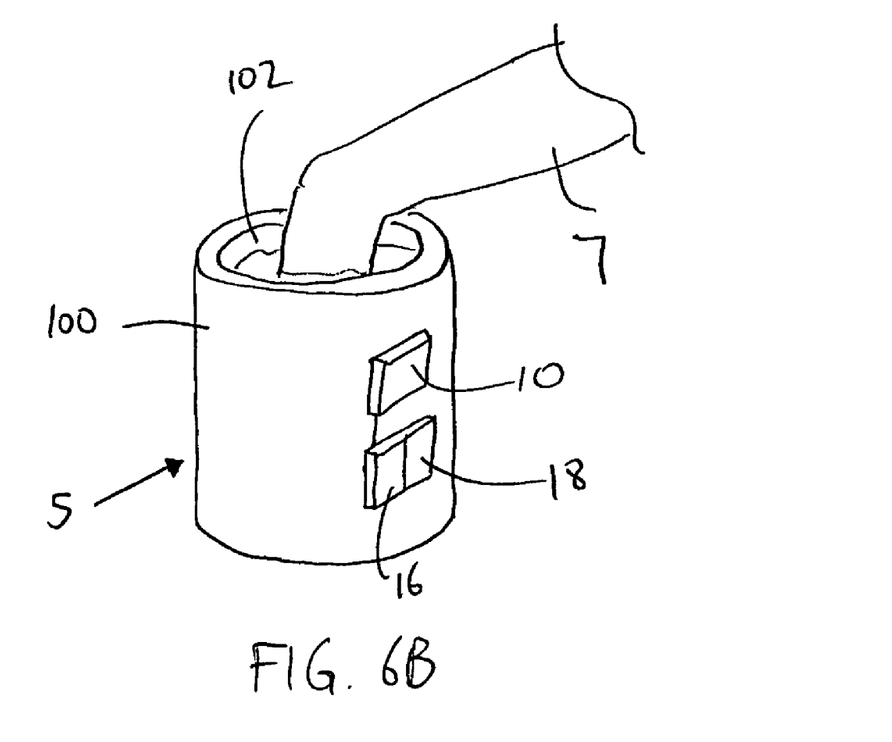
FIG. 6B illustrates the ultrasound system of FIG. 6A, showing the ultrasound system being used to treat a patient's leg.

In other embodiments, the structure 22 includes a container 100 having a lumen 102 sized to accommodate a least a portion of a limb of a patient (FIG. 6A). The ultrasound transducer 10 can be secured to an exterior surface or an interior surface of the container 100. During use, the container 100 is placed on a floor, and is filled with fluid. The patient's leg is then placed in the container 100 (FIG. 6B). Ultrasound is emitted from the transducer 10 and is transmitted through the fluid in the container 100 to reach the patient's leg.

In any of the embodiments described herein, the system 5 can further include one or more additional ultrasound transducer(s) 10 secured to the structure 22. The transducers 10 can be positioned in a side-by-side configuration to form a line. For example, in some embodiments, the system 5 includes two transducers 10, the center lines of which are spaced approximately two wavelengths (of the delivered acoustic wave) apart. Alternatively, the respective center lines of the transducers 10 can be spaced at other distances. For example, in some embodiments, the spaced distance can be selected such that the transducers 10 can provide a substantially uniform acoustic field at target tissue. In other embodiments, the transducers 10 can be positioned relative to each other to form other desired configurations. For example, in other embodiments, the system 5 includes two ultrasound transducers 10 that are positioned opposite from each other. For example, in the embodiments of FIG. 4A, in addition to the first transducer 10 that is secured to the second frame 62, the system 5 can further include a second transducer 10 secured to the first frame 60. As another example, in the embodiments of FIG. 6A, the system 5 can further include a second transducer 10 secured to the container 100 opposite from the first transducer 10. Providing a plurality of transducers 10 allows treatment of multiple target regions simultaneously. For example, in some embodiments, the system 5 includes three transducers 10 that are positioned relative to each other to form a line. Such configuration allows a substantial portion of a patient's calf to be treated by the system 5.

In some cases, the driver 16 and/or the controller 18 can be configured to control the transducers 10 such that acoustic waves emitted by the respective transducers 10 interact in a desired manner. For example, in some embodiments, a relative phase between transducers 10 may be varied. In one implementation, adjacent transducers 10 are alternately driven in phase and 180° out of phase. Because the acoustic fields from adjacent transducers 10 may overlap and because of resonance, the intensity distribution within a patient's body may form a series of interference maxima and mina. By altering the phase relation between the transducers 10, the locations of these pecks and nulls may be reversed, thereby providing overall uniform (or substantially uniform) insonification at target tissue 6. In other embodiments, the operating frequency of one or more transducers 10 may be varied to move an interference pattern of the acoustic field.

Figure 7:
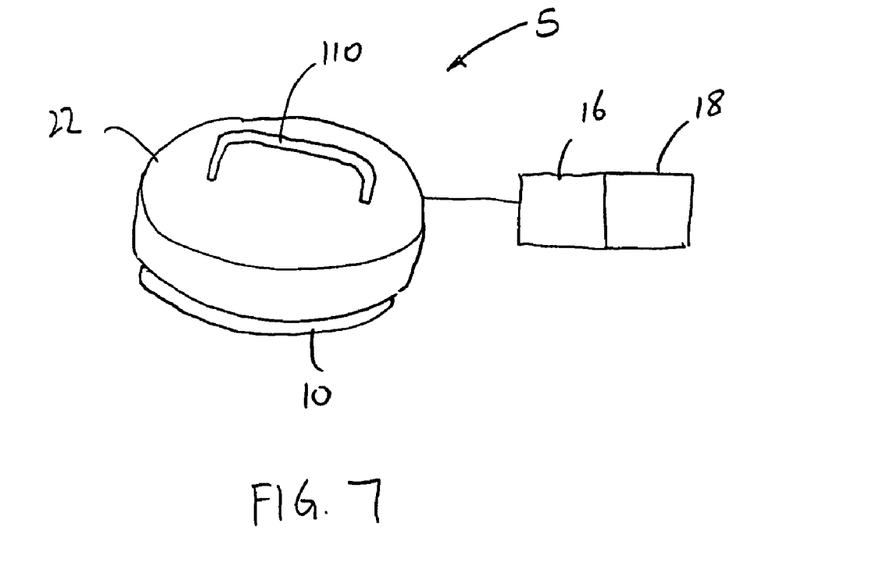
FIG. 7 illustrates an ultrasound system in accordance with other embodiments.

In other embodiments, the transducer 10 can be moveable relative to the patient 7. For example, in some embodiments, the system 5 further includes a handle 110 secured to the structure 22 (FIG. 7). During use, the handle 110 can be hold by a user and be used to press the transducer 10 (or the coupling membrane 30 if one is provided) towards a patient's skin.

Figure 8:
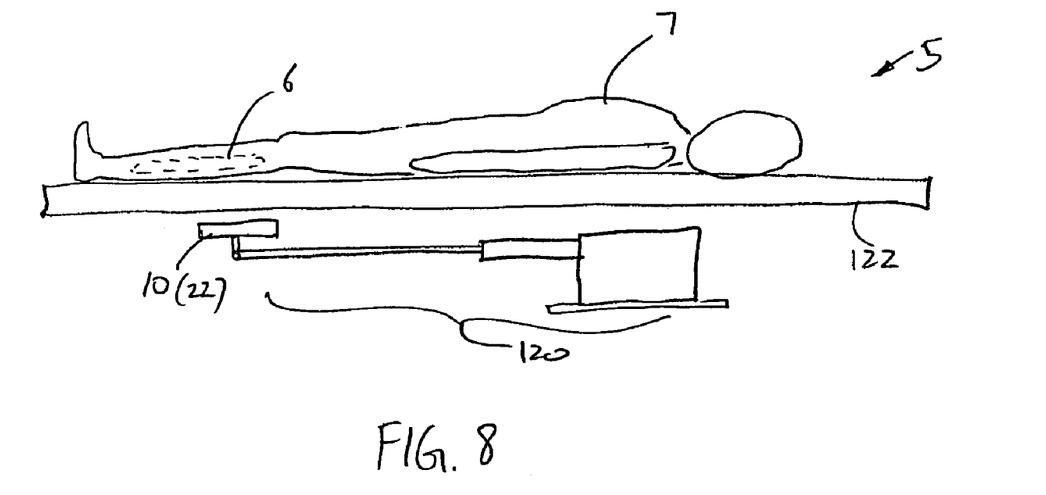
FIG. 8 illustrates an ultrasound system in accordance with other embodiments.

In other embodiments, The transducer 10 (or the structure 22) is secured to a mechanical linkage 120, such as a positioner, for adjusting a position of the transducer 10 relative to a patient support 122 (FIG. 8). During use, the mechanical linkage 120 positions the transducer 10 to aim the transducer 10 towards different regions of the patient 7, thereby allowing the transducer 10 to treat different portions of the patient 7. For example, the mechanical linkage 120 can translate and/or rotate the transducer 10 to thereby adjusting an aiming of the transducer 10. In some embodiments, the driver 16 and/or the controller 18 can be used to control positions of the transducer 10 in accordance with a prescribed treatment plan to thereby adjust the position, shape, and/or size of a focal zone.

Figure 9:
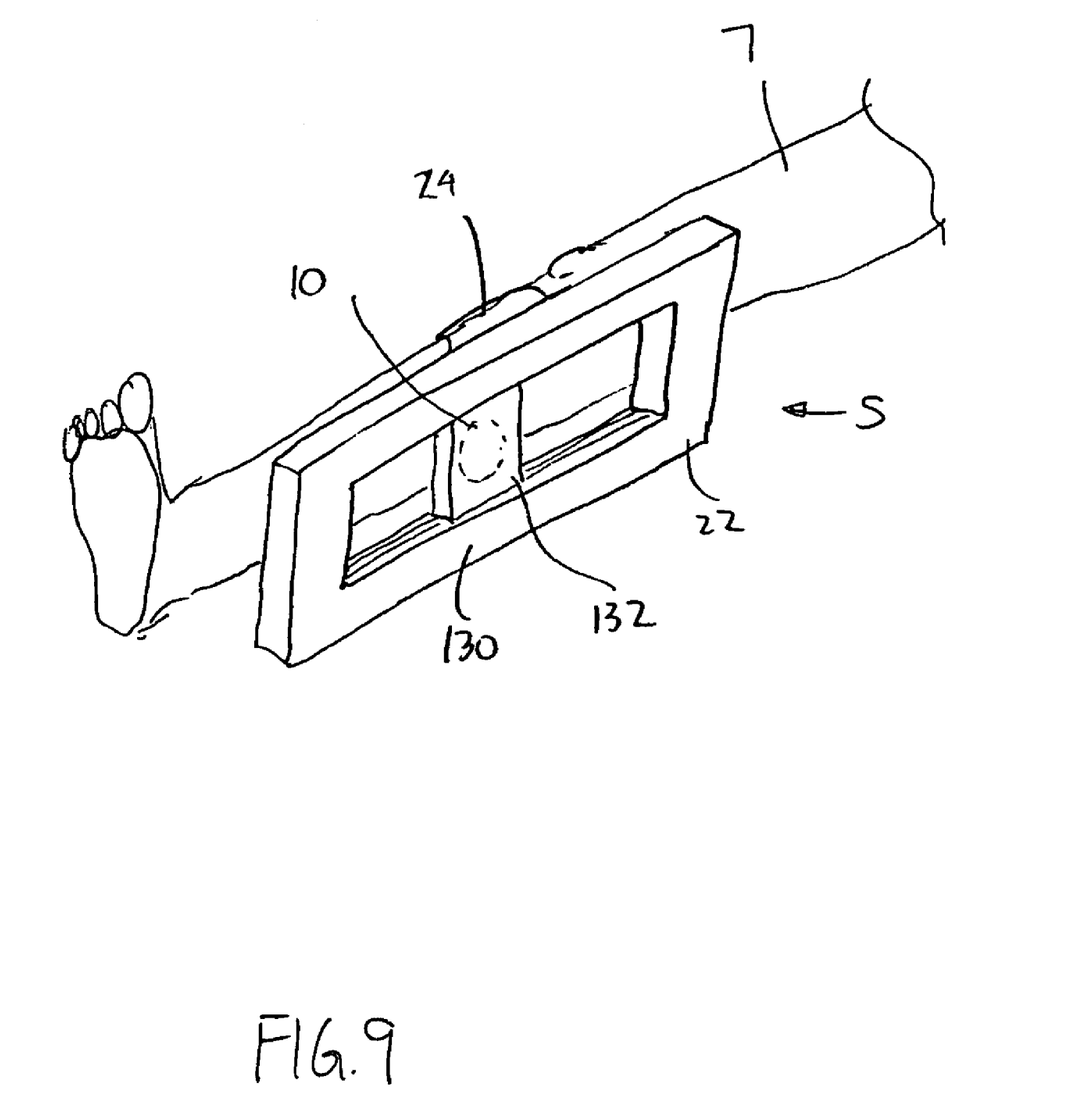
FIG. 9 illustrates an ultrasound system in accordance with other embodiments.

In other embodiments, the structure 22 includes a first portion 130 that can be secured relative to the patient 7 via the securing device 24, and a second portion 132 that is translatable relative to the first portion 130 (FIG. 9). In such cases, the system 5 includes one or more ultrasound transducer(s) 10 secured to the second portion 132. During use, the first portion 130 of the structure 22 is secured to the patient 7 via the securing device 24, and the second portion 132 is translated relative to the first portion 130 to thereby allow the transducer(s) 10 to treat different portions along the patient's leg. In some cases, such configuration allows an entire leg segment of the patient 7 to be treated. The positioning of the second portion 132 relative to the first portion 130 can be accomplished using a positioner, such as a motor. In some embodiments, the system 5 can further include a coupling membrane secured to the transducer(s) 10, as similarly discussed previously.

In any of the embodiments described herein, the system 5 further includes one or more hydrophones (not shown)

mounted either between the transducer(s) 10 and a patient's skin, or adjacent to the transducer(s) 10, for sampling acoustic field(s). This helps ensure proper electrical operation of the system 5 and coupling of the transducer 10.

In any of the embodiments described herein, the system 5 can further include a Doppler ultrasound device for measuring a degree of perfusion, which provides a qualitative measure of the increase in blood flow resulting from the ultrasound treatment provided by the system 5.

In any of the embodiments described herein, the system 5 can include a plesthysmography device, which is configured to restrict upper leg venous flow temporarily, and measure a rate of swelling of the lower leg, either by volume displacement or by circumferential increase in leg size. The measurement can then be used to determine an effect of the performed treatment.

Although particular embodiments have been shown and described, it should be understood that the above discussion is not intended to limit the present invention to these embodiments. It will be obvious to those skilled in the art that various changes and modifications may be made without departing from the spirit and scope of the present invention. For example, in other embodiments, instead of using the system 5 to treat a patient's leg, any of the embodiments of the system 5 described herein can be configured (e.g., shaped and/or sized) to treat other parts of a patient, such as an arm, a forearm, a thigh, a neck, or a chest, of a patient. Also, in other embodiments, instead of using the system 5 to treat ischemic limbs or tissue affected by peripheral arterial disease, any of the embodiments of the system 5 described herein can be used to treat other medical conditions in other embodiments. Further, in other embodiments, instead of placing the transducer 10 external to a patient, the transducer 10 can be placed inside a patient. For example, in some embodiments, the transducer 10 can be secured to a distal end of a probe, which is at least partially inserted inside a patient during use. In such cases, the transducer 10 delivers acoustic energy from within the patient. Thus, the present invention is intended to cover alternatives, modifications, and equivalents that may fall within the spirit and scope of the present invention as defined by the claims.

What is claimed:

1. A method of treating vascular tissue within a body, comprising:
    aiming an ultrasound transducer array towards target vascular tissue, the array comprising a plurality of transducers; and
    delivering ultrasound energy from the transducer array at a frequency that is between 20 kHz and 100 kHz towards the target vascular tissue, wherein adjacent transducers of the array are alternatively driven in phase and 180° out of phase to provide substantially uniform isonification of the target vascular tissue, and wherein the delivered ultrasound energy has an intensity selected to mechanically stimulate endothelial cells of the target vascular tissue to increase nitric oxide concentration within the target vascular tissue.

2. The method of claim 1, wherein the delivering is continued for at least 15 minutes.

3. The method of claim 1, further comprising placing the ultrasound transducer array externally to a patient.

4. The method of claim 3, wherein the ultrasound transducer array is secured to a limb of the patient.

5. The method of claim 1, wherein the ultrasound transducer array is secured to a probe, and the method further comprises inserting the probe at least partially within a patient.

6. An ultrasound system, comprising:
    a plurality of spaced apart ultrasound transducers configured to emit ultrasound energy from outside a patient to target vascular tissue located within the patient; and
    drive circuitry coupled to the plurality of spaced apart ultrasound transducers;
    wherein the drive circuitry is configured to generate a drive signal at a frequency that is between 20 kHz and 100 kHz for the plurality of spaced apart ultrasound transducers, the drive circuitry further being configured to drive adjacent transducers alternatively in phase and 180° out of phase so as to isonificate target vascular tissue in a substantially uniform manner with an enemy intensity selected to mechanically stimulate endothelial cells of the target vascular tissue.

7. The ultrasound system of claim 6, further comprising a controller coupled to the drive circuitry.

8. The system of claim 7, wherein the controller is configured to operate the spaced apart ultrasound transducers for a duration of at least 15 minutes.

9. The system of claim 8, wherein the controller is configured to operate the spaced apart ultrasound transducers for a duration less than 60 minutes.

10. The system of claim 6, further comprising a securing device for securing the plurality of ultrasound transducers relative to the patient.

11. The system of claim 10, wherein the securing device comprises a strap.

12. The system of claim 10, wherein the securing device comprises a first frame and a second frame containing the plurality of transducers that is moveable relative to the first frame so as to allow the plurality of transducers to treat different portions of vascular tissue.

13. The system of claim 6, further comprising a structure to which the plurality of ultrasound transducers are coupled, the plurality of ultrasound transducers moveable relative to the structure.

14. The system of claim 6, further comprising a support device for gravitationally supporting a portion of a patient, wherein the plurality of ultrasound transducers are coupled to the support device.

15. The system of claim 6, further comprising a container to which the plurality of transducers are secured, the container having a lumen, wherein the lumen has a cross-sectional dimension sized to accommodate at least a portion of a limb of a patient.

* * * * *

UNITED STATES PATENT AND TRADEMARK OFFICE
CERTIFICATE OF CORRECTION

PATENT NO. : 7,645,244 B2  Page 1 of 1
APPLICATION NO. : 11/178244
DATED : January 12, 2010
INVENTOR(S) : Mason et al.

It is certified that error appears in the above-identified patent and that said Letters Patent is hereby corrected as shown below:

At column 8, Claim 6, line 23, delete "enemy" and insert therefore --energy--

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,645,244 B2 Page 1 of 1
APPLICATION NO. : 11/178244
DATED : January 12, 2010
INVENTOR(S) : Mason et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1076 days.

Signed and Sealed this

Sixteenth Day of November, 2010

David J. Kappos
*Director of the United States Patent and Trademark Office*